United States Patent [19]

Metz et al.

[11] Patent Number: 5,227,531
[45] Date of Patent: Jul. 13, 1993

[54] PROCESS FOR THE PREPARATION OF FLUOROBENZALDEHYDES

[75] Inventors: Hans J. Metz, Heppenheim; Klaus Warning, Eppstein/Taunus, both of Fed. Rep. of Germany

[73] Assignee: Hoechst Aktiengesellschaft, Frankfurt am Main, Fed. Rep. of Germany

[21] Appl. No.: 711,365

[22] Filed: Jun. 5, 1991

Related U.S. Application Data

[63] Continuation of Ser. No. 114,536, Oct. 29, 1987, abandoned.

[30] Foreign Application Priority Data

Oct. 31, 1986 [DE] Fed. Rep. of Germany ....... 3637156

[51] Int. Cl.$^5$ ............................................... C07C 45/00
[52] U.S. Cl. ..................................... 568/433; 568/437
[58] Field of Search ................................ 568/433, 437

[56] References Cited

U.S. PATENT DOCUMENTS

| | | |
|---|---|---|
| 3,654,349 | 4/1972 | Shen et al. . |
| 3,725,548 | 4/1973 | Shen et al. . |
| 3,787,489 | 1/1974 | Antoni et al. . |
| 3,833,581 | 9/1974 | MacKenzie et al. ................ 568/433 |
| 4,579,976 | 4/1986 | Cheminal et al. ................... 568/466 |

FOREIGN PATENT DOCUMENTS 0164619 12/1985 European Pat. Off. .
0117100 12/1986 European Pat. Off. .

OTHER PUBLICATIONS

Miller, *Aromatic Nucleophilic Substitution,* Elsevier, Amsterdam, 1968, p. 79.
Morrison et al., *Organic Chemistry,* 3rd Ed., Allyn and Bacon, Inc. Boston, 1977, pp. 633, 643-644.
Yakobson et al., *Synthesis,* 1983, 169-170.
Weygand, Preparative Organic Chemistry, John Wiley & Sons, N.Y., 1972, p. 209.

*Primary Examiner*—Arthur C. Prescott

[57] ABSTRACT

A process for the production of fluorobenzaldehydes which comprises reacting a chlorobenzaldehyde with an alkali fluoride in a dipolar aprotic medium.

20 Claims, No Drawings

PROCESS FOR THE PREPARATION OF FLUOROBENZALDEHYDES

This is a continuation of our co-pending application Ser. No. 07/114,536, filed Oct. 29, 1987, now abandoned.

Fluorobenzaldehydes are compounds which are derived from benzaldehyde $C_6H_5CHO$ by replacing one or more hydrogen atoms of the $C_6H_5$ group by fluorine atoms and, optionally, also by other substituents in addition. They are mainly intermediate products, for example, in the preparation of pharmaceutical products and crop protection agents.

Various processes are known for the preparation of fluorobenzaldehydes. Thus, for example, German Auslegeschrift 2,039,426 (Example 7) describes the preparation of 2,4-and 3,4-difluorobenzaldehyde in 70 and 76% yield respectively; the reaction proceeds according to the following formulation:

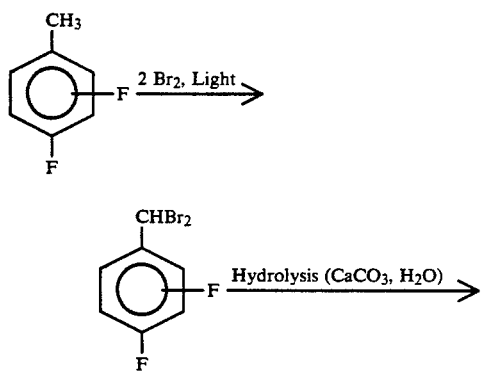

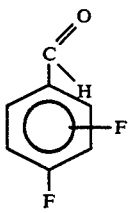

According to EP-A-0,117,100 (Preparation 3, page 16), 2,4-difluorobenzaldehyde is obtained in good yield also by the following path:

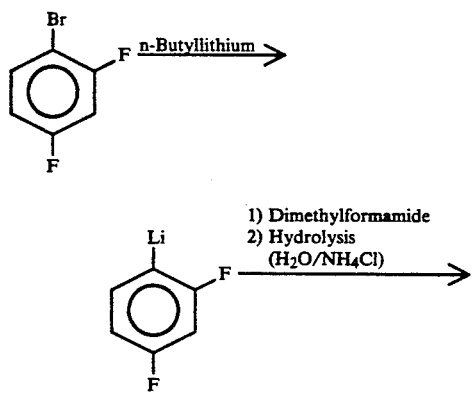

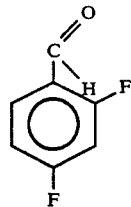

The starting products for these reactions can be obtained, for example, by a single or multiple Balz-Schiemann reaction. The term "Balz-Schiemann reaction" is understood to mean the thermal decomposition of aromatic diazonium tetrafluoroborates to the corresponding aromatic fluorine compounds. The formulation, for example, for the preparation of 2,4-difluorotoluene, may be reproduced as follows:

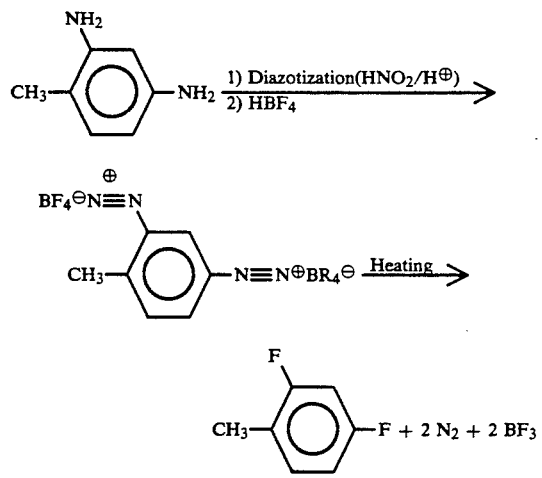

Starting from common starting products, these processes consequently involve multi-stage syntheses, the hydrolysis stages of which result in the formation of salt-containing and consequently environment polluting waste waters. In addition, the preparation by means of n-butyllithium requires special safety measures (because of the spontaneous inflammability of the latter in air).

Another preparation method for fluorobenzaldehydes is the subject of EP-A-0,164,619. According to the latter, chlorobenzonitriles or chlorobenzoyl halides are reacted with KF at elevated temperature in a dipolar aprotic solvent, in particular sulfolane (=tetrahydrothiophen-S,S-dioxide), and the fluorobenzonitrile or fluorobenzoyl halide respectively obtained is optionally converted in a manner known per se into other aromatic fluoro compounds, inter alia, also into fluorobenzaldehydes. Consequently, 2,4,5-trifluorobenzaldehyde is obtained by first reacting 2,4,5-trichlorobenzonitrile with 3 KF to form 2,4,5-trifluorobenzonitrile and then proceeding as follows, the specified path from the fluorinated nitrile to the aldehyde corresponding to the reaction sequence described on page 6 of the EP-A:

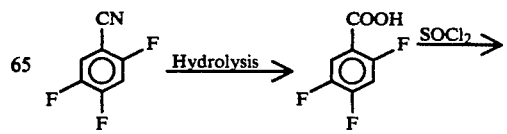

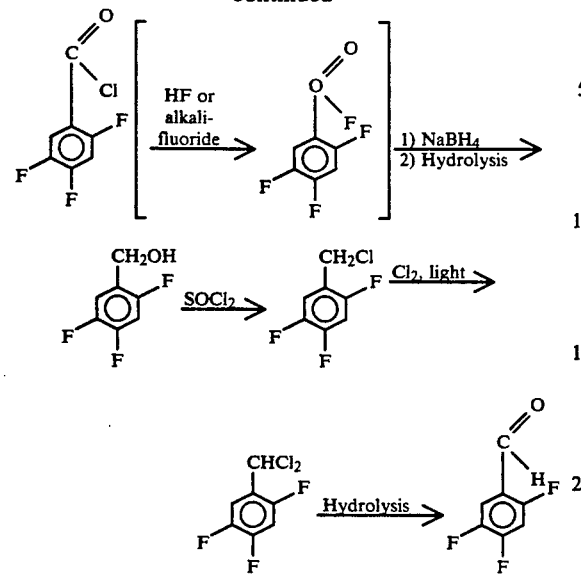

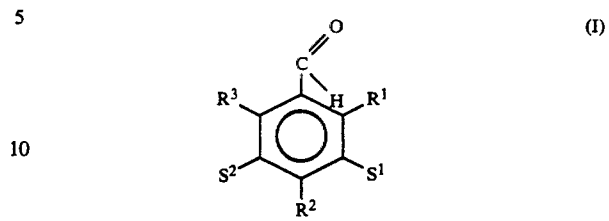

As is evident, this synthesis requires a multiplicity of reaction steps.

In the effort to provide a simpler preparation method for fluorobenzaldehydes, it has now been found that this object is achieved by reacting chlorobenzaldehydes with alkali fluorides in an aprotic reaction medium. The object of the invention is therefore a process for the preparation of fluorobenzaldehydes by applying the chlorine/fluorine exchange reaction to aromatic compounds using alkali fluoride in dipolar aprotic medium; this process is a process wherein chlorobenzaldehyde is used for said chlorine/fluorine exchange reaction. The aldehyde yields in this case are normally around about 70% and over. Starting from common starting products, the process provides a simple and single-stage synthesis method for fluorobenzaldehydes, which method produces no waste water.

The achievement of this reaction is extremely surprising because, according to the abovementioned EP-A-0,164,619, it had to be assumed that fluorobenzaldehydes cannot be prepared in a single reaction stage from the corresponding chlorobenzaldehydes by chlorine/fluorine exchange using alkali fluoride in an aprotic medium, but that fluorobenzaldehydes can only be prepared in a fairly costly manner in several reaction steps from those chlorinated aromatic compounds which have no CHO group. This also appears understandable because alkali fluorides are known as strong bases in an aprotic medium in which, in contrast to aqueous systems, virtually no solvation of the fluoride occurs (cf. the review by G. G. Yakobson and N. E. Akhmetova in Synthesis, 1983, pages 169 and 170 (". . . alkali metal fluorides are rather strong bases . . . ", cf. page 169, left-hand column, paragraph 1 and page 170, paragraph 2: "The basic properties of alkali metal fluorides were first revealed in dehydrohalogenation reactions")). However, aldehydes are known to be by no means stable towards strong bases. A reaction of aldehydes with bases is, for example, the so-called Cannizzaro reaction (Oxidation-reduction of aldehydes in the presence of bases). A reaction with the activated hydrogen atoms in the $\alpha$ position with respect to CO, SO or SO$_2$ groups of the aprotic solvent used is also conceivable.

To carry out the reaction, all the possible chlorobenzaldehydes can in principle be used; preferred is the use of chlorobenzaldehydes of formula (I)

$$\text{(I)}$$

in which $R^1$, $R^2$ and $R^3$ represent, independently of each other, H, F and/or Cl, but at least one of the radicals is chlorine and at least one of the radicals $R^1$ and $R^3$ is hydrogen, and $S^1$ and $S^2$, independently of each other, =H and/or are radicals which reduce the electron density on the benzene ring, preferably =H.

Exemplary $S^1$ and $S^2$ radicals which reduce the electron density on the benzene ring by mesomeric or inductive effects (cf. Organikum VEB, published by Deutscher Verlag der Wissenschaften, 1973, sections 5.1.2 and 5.2.1) are —NO$_2$, —CN and —CHO.

Exemplary starting compounds for the reaction according to the invention are therefore o-, m- and p-chlorobenzaldehyde, 2,4-dichloro, 2,4,6-trichlorobenzaldehyde, 2,4-dichloro-3-nitrobenzaldehyde, 2-chloro-4-fluoro- and 2-fluoro-4-chlorobenzaldehyde, it being possible also to use the latter as a mixture, especially as the result in a uniform final product. A particularly preferred starting compound is 2,4-dichlorobenzaldehyde.

For the exchange of the chlorine atoms in the starting compound, 1 mol of alkalifluoride is stoichiometrically required per chlorine atom. If it is intended to exchange all the chlorine atoms in the starting chlorobenzaldehyde, it is advantageous to use up to about 200%, in particular about 100–120% of the stoichiometric quantity of alkali fluoride. The use of larger alkali fluoride quantities is possible but does not offer any particular advantage.

In the case of benzaldehydes containing several chlorine atoms, the reaction may be carried out in a manner such that a predominantly partially fluorinated product is produced by using a smaller quantity of alkali fluoride in the reaction than is required for the exchange of all the chlorine atoms.

As alkali fluoride, use is made, for example, of sodium fluoride or of alkali fluorides on their own or as mixtures with the simple alkali fluorides. Preferred, however, is potassium fluoride or a mixture of the latter with rubidium and/or cesium fluoride in any desired molar ratio; particularly preferred is a mixture containing only a small (catalytic) proportion of rubidium and/or cesium fluoride (up to about 5 mol-%).

Suitable as solvents for the reaction are in principle all the possible dipolar aprotic solvents, preferably tertiary carboxylic acid amides such as dimethylformamide, dimethylacetamide, N-methylpyrrolidone, N,N,N',N'-tetramethylurea, N,N'-dimethylimidazolidin-2-one, sulfoxides such as dimethylsulfoxide and sulfones such as dimethylsulfone, diphenylsulfone and sulfolane. Particularly preferred are N-methylpyrrolidone, dimethylsulfoxide and dimethylsulfone, in particular, however, solfolane. The solvents can be used both individually and also mixed with each other.

The initial concentration of the aldehyde may be in a wide range; preferably, it is about 0.5-3 mol/kg of solvent, in particular about 1-1.7 mol/kg of dipolar aprotic medium (solvent).

The reaction is able to proceed in a wide temperature range. Expediently, temperatures between about 120° and 250° C., in particular between about 180° and 230° C., are employed.

The reaction according to the invention is preferably carried out in a manner such that the starting chlorobenzaldehyde is heated with the solvent and the alkali fluoride for a prolonged time while stirring and in a protective gas atmosphere, for example, argon, preferably, however, nitrogen. The course of the reaction is monitored, for example, by gas chromatography. After the desired degree of conversion has been reached, the product is worked up: preferably, the inorganic part (alkali halide) is separated off by filtering off under an inert gas atmosphere. The product contained in the organic phase is then purified, preferably by rectification under reduced pressure.

The invention is explained in more detail by the examples below, all operations being carried out under $N_2$ as protective gas.

EXAMPLES 1) 175 g (1 mol) of 2,4-dichlorobenzaldehyde were heated together with 1,000 g of sulfolane and 151 g (2.6 mol) of potassium fluoride for 15 h at 210°-215° C. The reaction mixture was thoroughly mixed during the entire duration of the reaction by a powerful stirring mechanism in order to prevent the insoluble salts settling. Cooling was then carried out to room temperature and the inorganic constituents were separated off by means of a suction filter covered with a blanket of nitrogen. Rinsing was carried out twice using 100 g of fresh sulfolane in each case. From the filtrate 96.6 g=68% of theory of 2,4-difluorobenzaldehyde with a boiling point of 70.5° C. (40 mbar) was obtained by rectification under reduced pressure in a column containing approx. 20 theoretical trays. Solidification point: approximately 2° C.

2) 56 g (0.4 mol) of 4-chlorobenzaldehyde were heated together with 200 g of 1,3-dimethylimidazolidin-2-one, 29.5 g of potassium fluoride and 4.03 g of cesium fluoride (5 mol-% referred to potassium fluoride) at 215° C. for 20 h while stirring vigorously. 12.7% by weight (32.4 g) of 4-fluorobenzaldehyde, which is equivalent to 65.2%, and 4.3% by weight (=11.0 g) of 4-chlorobenzaldehyde, which is equivalent to 19.6%, referred in each case to the starting material, were detected by gas chromatography in the reaction mixture. The working up was carried out as described in Example 1.

3) 158.5 g (1 mol) of a mixture of 56% of 4-chloro-2-fluoro-benzaldehyde and 44% of 2-chloro-4-fluorobenzaldehyde were heated together with 700 g of sulfolane and 75 g (1.29 mol) of potassium fluoride at 215° C. for 10 h. The working up was carried out as in Example 1. 99.5 g of 2,4-difluorobenzaldehyde equivalent to 70% of the feed-stock was obtained.

We claim:

1. A process for the production of fluorobenzaldehydes which comprises reacting a chlorobenzaldehyde free from an-$NO_2$ substituent with an alkali fluoride in a dipolar aprotic medium.

2. A process as claimed in claim 1, wherein both $S^1$ and $S^2$ and at least one of $R^1$ and $R^3$ represent hydrogen.

3. A process as claimed in claim 2, wherein the chlorobenzaldehyde is 2,4-dichlorobenzaldehyde.

4. A process as claimed in claim 1, wherein the alkali fluoride is employed in an amount between the stoichiometric amount and up to 200%, related to the stoichiometric amount necessary for replacing all chlorine atoms of the chlorobenzaldehyde.

5. A process as claimed in claim 4, wherein the amount of the alkali fluoride is in the range from about 100 to 120% of the stoichiometric amount necessary for replacing all chlorine atoms.

6. A process as claimed in claim 1, wherein the alkali fluoride is employed in a smaller amount than is necessary for the replacement of all chlorine substituents, to yield a partially fluorinated product only.

7. A process as claimed in claim 1, wherein the alkali fluoride employed is potassium fluoride.

8. A process as claimed in claim 1, wherein a mixture of potassium fluoride and at least one fluoride of rubidium and cesium is applied.

9. A process as claimed in claim 8, wherein the total amount of the fluorides of rubidium and cesium is at most 5 mol-%.

10. A process as claimed in claim 1, wherein the dipolar aprotic medium is a tertiary amide of a carboxylic acid, a sulfoxide or a sulfone or a mixture thereof.

11. A process as claimed in claim 10, wherein the dipolar aprotic medium is N-methylpyrrolidone.

12. A process as claimed in claim 10, wherein the dipolar aprotic medium is at least one of dimethylsulfoxide and dimethylsulfone.

13. A process as claimed in claim 10, wherein the dipolar aprotic medium is sulfolane.

14. A process as claimed in claim 1, which is carried out at a temperature in the range from about 120° to 250° C.

15. A process as claimed in claim 14, which is carried out at a temperature in the range from about 180° to 230° C.

16. A process as claimed in claim 1, wherein the initial concentration of the aldehyde is in a range from about 0.5 to 3 mol/kg of dipolar aprotic medium.

17. A process as claimed in claim 16, wherein the initial concentration of the aldehyde is in the range from about 1 to 1.7 mol/kg of dipolar aprotic medium.

18. A process as claimed in claim 1 which is carried out under a protective gas.

19. A process as claimed in claim 1, wherein the chlorobenzaldehyde has the formula

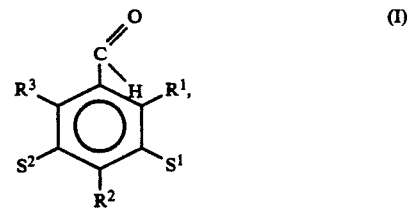

wherein $R^1$, $R^2$ and $R^3$ each are equal or different and are hydrogen, fluorine or chlorine, at least one being however chlorine and $S^1$ and $S^2$ are equal or different and represent hydrogen or —CHO.

20. A process for the production of a fluorobenzaldehyde which comprises reacting a mono-, di- or trichlorobenzaldehyde starting material with an alkali fluoride in a dipolar aprotic medium, whereby at least one of the chlorine substituents of the mono-, di- or trichlorobenzaldehyde starting material is replaced with a fluorine substituent, said mono-, di- or trichlorobenzaldehyde starting material having the formula
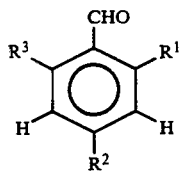
wherein $R^1$, $R^2$ and $R^3$ each are equal or different and are hydrogen, fluorine or chlorine, at least one however being chlorine.